United States Patent [19]
Gokhfeld

[11] Patent Number: 5,792,938
[45] Date of Patent: Aug. 11, 1998

[54] HUMIDITY SENSOR WITH DIFFERENTIAL THERMAL DETECTION AND METHOD OF SENSING

[75] Inventor: Yuzef Gokhfeld, Waltham, Mass.

[73] Assignee: Panametrics, Inc., Waltham, Mass.

[21] Appl. No.: 764,180

[22] Filed: Dec. 13, 1996

[51] Int. Cl.$^6$ .................................................. G01N 19/10
[52] U.S. Cl. ........................................ 73/29.02; 73/335.05
[58] Field of Search ..................... 73/335.05, 29.09, 73/29.02, 335.02, 335.03, 335.04; 374/28

[56] References Cited

U.S. PATENT DOCUMENTS

| | | | |
|---|---|---|---|
| 3,523,244 | 8/1970 | Goodman et al. | 324/61 |
| 3,539,917 | 11/1970 | Chleck | 324/61 |
| 4,143,177 | 3/1979 | Kovac et al. | 427/79 |
| 4,203,087 | 5/1980 | Kovac et al. | 338/35 |
| 4,277,742 | 7/1981 | Kovac et al. | 324/61 |
| 4,419,021 | 12/1983 | Terada et al. | 73/336.5 X |
| 4,568,875 | 2/1986 | Piso et al. | 324/61 |
| 4,677,416 | 6/1987 | Nishimoto et al. | 73/336.5 X |
| 4,751,654 | 6/1988 | Lyyra | 364/482 |
| 4,877,329 | 10/1989 | Sauerbaum et al. | 374/28 |
| 5,027,077 | 6/1991 | Yanagisawa et al. | 73/336.5 X |
| 5,033,284 | 7/1991 | Belt et al. | 73/23.21 X |
| 5,156,045 | 10/1992 | Ponkala | 73/170 |
| 5,235,267 | 8/1993 | Schöneberg et al. | 324/71.5 |
| 5,274,334 | 12/1993 | Mills | 324/678 |
| 5,364,185 | 11/1994 | VanZandt et al. | 73/29.02 X |
| 5,485,747 | 1/1996 | Antikainen et al. | 73/335.03 |
| 5,511,418 | 4/1996 | Antikainen et al. | 73/335.03 |
| 5,614,671 | 3/1997 | Morissey | 73/335.05 |
| 5,644,080 | 7/1997 | Stormbom et al. | 73/335.05 |

OTHER PUBLICATIONS

NIST Research for Industry, "Microsensors Sniff out Gases," *Technology at a Glance*, p. 3, Fall 1996.

*Primary Examiner*—Hezron E. Williams
*Assistant Examiner*—Jay L. Politzer
*Attorney, Agent, or Firm*—Lahive & Cockfield, LLP

[57] ABSTRACT

A method of humidity measurement wherein a humidity responsive element is subjected to the measuring environment and its temperature coefficient is measured. A system operates a sensor element between a first temperature and a second temperature, determining its temperature coefficient, which is then compared to a previously compiled table. The differential measurement thus made automatically corrects for system error originating in equipment drift, cable capacitance change and various aging and slow hysteresis or sensor capacitance variations. In another embodiment, an occasional differential measurement is performed to detect errors in a set of stored curves and update the tables used for single-point humidity measurements, thus obviating the need for protocols involving reference gases or recalibration.

16 Claims, 6 Drawing Sheets

PRESSURE OF AQUEOUS VAPOR

VAPOR PRESSURE OF ICE

PRESSURE OF AQUEOUS VAPOR OVER ICE
IN mm OF Hg

| TEMP. °C | 0.0 | 0.2 | 0.4 | 0.6 | 0.8 |
|---|---|---|---|---|---|
| 0 | 4.579 | 4.647 | 4.715 | 4.785 | 4.855 |
| 1 | 4.926 | 4.998 | 5.070 | 5.144 | 5.219 |
| 2 | 5.294 | 5.370 | 5.447 | 5.525 | 5.605 |
| 3 | 5.685 | 5.766 | 5.848 | 5.931 | 6.015 |
| 4 | 6.101 | 6.187 | 6.274 | 6.363 | 6.453 |
| 5 | 6.543 | 6.635 | 6.728 | 6.822 | 6.917 |
| 6 | 7.013 | 7.111 | 7.209 | 7.309 | 7.411 |
| 7 | 7.513 | 7.617 | 7.722 | 7.828 | 7.936 |
| 8 | 8.045 | 8.155 | 8.267 | 8.380 | 8.494 |
| 9 | 8.609 | 8.727 | 8.845 | 8.965 | 9.086 |
| 10 | 9.209 | 9.333 | 9.458 | 9.585 | 9.714 |
| 11 | 9.844 | 9.976 | 10.109 | 10.241 | 10.380 |
| 12 | 10.518 | 10.658 | 10.799 | 10.941 | 11.085 |
| 13 | 11.231 | 11.379 | 11.528 | 11.680 | 11.833 |
| 14 | 11.987 | 12.144 | 12.302 | 12.462 | 12.624 |
| 15 | 12.788 | 12.953 | 13.121 | 13.290 | 13.461 |
| 16 | 13.634 | 13.809 | 13.987 | 14.166 | 14.347 |
| 17 | 14.530 | 14.715 | 14.903 | 15.092 | 15.284 |
| 18 | 15.477 | 15.673 | 15.871 | 16.071 | 16.272 |
| 19 | 16.477 | 16.685 | 16.894 | 17.105 | 17.319 |

USE TEMPERATURES LISTED AS:

DEW POINTS
FROST POINTS
AMBIENT OR ACTUAL GAS TEMPS.

USE VALUES LISTED FOR:

P (PARTIAL PRESSURE $H_2O$)
$P_S$ (SATURATED VAPOR PRESSURES)

HUMIDITY SENSOR WITH DIFFERENTIAL THERMAL DETECTION AND METHOD OF SENSING

BACKGROUND

This invention relates in general to the measurement of water vapor or dew point in a gas, and more particularly to such measurement using a compact solid state sensor which provides rapid measurement of absolute humidity or dew point over a wide range of temperature and pressure conditions.

The technique for performing a measurement of this sort has evolved, from the nineteenth century approach of plotting the temperature differential between dry and wet bulb thermometers, to modern systems wherein a small well-defined circuit element or structure which changes its resistance or capacitance in response to the surrounding humidity, is adapted to sense humidity in diverse process or measurement environments. By making the active circuit element thin or small, one is able to provide an instrument which reaches equilibrium with the atmosphere relatively quickly, and by utilizing films of material such as polymer or ceramic, these instruments may be relatively long-lived, such that the compilation of a table of operating parameters is readily carried out and can remain in effect or be recalibrated to achieve accuracy, or at least repeatability, for extended periods of time.

One example of this approach to humidity sensing instrumentation is shown in U.S. Pat. No. 3,523,244. That patent shows a sensor element in which an aluminum oxide layer approximately one quarter of a micron thick is formed on a conductive substrate and covered with a thin conductive but porous top surface electrode. The oxide layer, a hard hydrated form of aluminum oxide with an irregular pore structure, allows water vapor to permeate or diffuse through its thickness. This material takes on water in proportion to its partial pressure in the surrounding atmosphere, and changes in both its resistance and its capacitance are readily measured between the substrate and the surface electrode. As noted above, because of the relatively small thickness of the active layer, the element responds quickly to the surrounding humidity, with a response time normally ranging from a fraction of second to several minutes, depending on degree of saturation, and has a wide range for humidity levels that change over a range of three or more orders of magnitude.

Readout of such a device is accomplished with conventional circuitry of the type used for a great number of capacitive or resistive sensors, such as load cells, diaphragm-type capacitive differential pressure measuring instruments, and others. This may be done with a capacitance measuring bridge, or other such circuit. For example, a square or sawtooth wave oscillation of a few hundred to a few thousand Hz may be provided across the element to cyclically charge and discharge the sensor, and the voltage developed on the sensor may be synchronously sampled, amplified, rectified, and output as a normalized (e.g., zero to one volt) signal. In various embodiments, the direct voltage readout may be strictly proportional to absolute humidity or otherwise reflect the humidity reading in a particularly simple fashion. More generally, the capacitance will vary both with humidity and with temperature of the element, and readout is accomplished by having first compiled a table of the output values, and stored the table, and then applying the correct calibration scale from the stored table for the given temperature, pressure or other directly measured condition.

In addition to hydrated ceramic films as described in the above-referenced '244 patent, a number of films of a polymer, such as a polysulphone film, and other materials have been used as the water-sensitive layer to enhance the response, stability or other characteristics of the sensor.

One method for using such sensors is to first obtain a sensor calibration curve of the sensor capacitance for each relative humidity at a fixed temperature. Then, when a sample gas with an unknown relative humidity or dew point is applied to the sensor and the corresponding capacitance value is measured, the unknown relative humidity can be found by finding the corresponding value on the previously compiled capacitance versus relative humidity calibration curve. When the relative humidity and sensor temperature are both known, the corresponding dew point is also uniquely determined and may be found or interpolated empirically from widely available tables of saturated water vapor pressure versus temperature. However, since the sensor is in general quite small, the above methodology implicitly measures the sensor capacitance or resistance at the temperature of the test gas, and this requires that the calibration curve be obtained and stored for all temperature levels at which the element is to be used.

While in theory this measurement can be made quite accurate, in practice, a number of possible sources of error are inherent in the methodology. First, any temperature detection error leads to reliance on an inappropriate calibration curve. Second, as a practical matter calibration curves are compiled at the time the sensor is built or installed, so that sensor "aging" over time may cause its characteristics to depart from those originally measured. Third, some hysteresis error may arise because the process of detection relies on the absorption or desorption of water from the thin layer, and the driving forces for the mechanics of equilibration may be affected by the previous level of humidity measured, so that the calibration curve will depend on the previous relative humidity and the time interval during which the new and different level has been applied to the sensor. This memory effect may last for days or weeks. Furthermore, systematic errors of the measuring instrument such as errors in capacitance measuring bridges, in volt meters, parasitic capacitance of connecting cables, or changes in capacitance due to bending or realignment of wires, or other changes in circuit parameters that occur with temperature, may all contribute to inaccuracies of the fundamental signals or of their conversion to humidity measurements.

A number of these sources of error can be overcome in a sophisticated measurement environment by processes of recalibrating or reinstalling the equipment, protocols for baking out or zeroing the sensor, and by initializing or purging processes such as applying a reference dry gas for a known period of time, or other processes which may be specific to the sensor or electronics under consideration. Furthermore when operated with a microprocessor-controlled circuit, as is commonly done, tables of normal aging characteristics may be built into the device, allowing an estimated correction factor to be applied for some of these effects.

Overall it may be said that the development of solid state humidity sensors and associated instrumentation have led to relatively hardy and compact embodiments capable of making repeated measurements, but these measurements, because of the underlying physics of the sensor and electrical signal processing, possess limitations that should be addressed.

It would therefore be desirable to provide a humidity sensor of enhanced accuracy, stability or ease of calibration.

SUMMARY OF THE INVENTION

This is achieved in accordance with a method of humidity measurement of the present invention wherein a humidity responsive element is subjected to the measuring environment and its thermal capacitance or resistance coefficient is measured. A representative device operates by cycling the sensor element between a first temperature and a second temperature and determining the sensor capacitance at each temperature. The sensor capacitance difference, or thermal coefficient of capacitance, is then compared to a previously compiled table of gas dew point versus capacitance increment calibration curves. The differential measurement thus made is free from systematic error originating in equipment drift, cable capacitance change and various aging and slow hysteresis or sensor capacitance variations. Furthermore, initial calibration requires only a set of $\Delta C$ curves rather than a full matrix of calibration points.

In one embodiment, a capacitive type relative humidity sensor is placed in thermal contact with an electric heater, a thermoelectric cooler, or both, and the heater and/or cooler are operated to drive the sensing element from a first temperature to a second temperature which is preferably done under control of a digital device such as a microprocessor control chip, or under control of simple analog devices such as thermal cut-off or cut-in switches. Depending on the ambient temperature, the device may return to its initial temperature passively, or be actively driven by the heater or cooler. The frequency or cycle time of these temperature changes is selected to correspond to the time constant of the sensor in the ranges of temperature and relative humidity of the intended sample gas, and measurement is preferably made at each temperature end point. In illustrative embodiments, a platinum film may be deposited in or on the substrate below the sensing film and energized at a controlled power level to heat the film. A Peltier device may be employed as the cooler. These are driven to change the sensor temperature and effect upper and lower readings, with a time constant or cycle time of approximately 1–3 minutes, or may operate at greater intervals or a more prolonged period of time, depending on the measurement protocol.

In one preferred measurement protocol, a fixed cycle time is employed, and capacitance is measured at lower and upper temperatures successively in each cycle with the sensor immersed in the sample environment. The measured capacitance difference is then compared to that of a previously compiled table of $\Delta C$ vs. dew point for a range of dew point values.

In another measurement protocol a more prolonged interval elapses between $\Delta C$ differential measurements, and during the interval conventional measurements are employed to determine moisture content. Effectively, recalibration is done by measuring the capacitance C of separate or preferably the same humidity sensor employed in the $\Delta C$ measurement as described above at a fixed or continuously monitored (i.e., measured) temperature to compile a new calibration table which is corrected by the more accurate $\Delta C$ measurement. The updated C vs. dew point table so obtained is then used alone for a time, applying a standard conversion procedure to determine dew point measurement result.

Both measurements (i.e., the conventional one based on C measurement, and $\Delta C$ differential measurement in accordance with this invention) are assumed to be made practically at the same time and with the same gas portion, so humidity data obtained from each single $\Delta C$ differential measurement is sufficient to provide one point calibration of the conventional C vs. dew point calibration curve. In other words, the same current value of sample gas humidity is simultaneously measured by two different methods, a $\Delta C$ differential measurement method to determine the correct calibration curve, followed by a one point C measurement and look up, in the conventional manner, on a stored humidity curve. The conventional method is then used for some time alone e.g. over a period of hours or days, after which another $\Delta C$ difference measurement result is obtained and used for another calibration as described above.

The $\Delta C$ differential measurement is readily performed in a very short time, e.g., within a 5 to 15 second time interval, so this automatic calibration is practically transparent i.e., not noticeable and does not delay the conventional method of humidity measurement. In this embodiment, the time period between calibrations depends on the time period during which the conventional measurement remains stable, e.g., one hour.

The invention also contemplates that a more sophisticated algorithm be embodied into a microprocessor based controller. By way of example, the $\Delta C$ different measurement protocol can be temporarily omitted as long as change in the consecutive conventional measurements remains less than a preset threshold. This minimizes $\Delta C$ differential measurement dynamic error.

In one embodiment of a device for carrying out the method, a heater is provided to heat the sensor and the sensor is operated in two cycles or at two different power levels to drive the sensor to a first temperature $T_1$ above ambient temperature, and to a second higher, temperature $T_2$. The temperature then returns to $T_1$ by passive cooling, and is again driven to $T_2$. In another embodiment a Peltier cooler is placed in thermal contact with the sensor, and it is operated to decrease the temperature of the sensor element to one or more levels $T_{-1}$, $T_{-2}$ below ambient. Again, the sensors return to the higher temperature by passive interaction with the surroundings. In yet a third embodiment the system includes both a heater and a cooler, and the sensor element is actively driven between the two temperatures at which its capacitance is measured. By actively driving the device to $T_1$, then to $T_2$, then back to $T_1$ in a known cycle time, the memory effects are made repeatable, and are a function of the cycling conditions which are accurately represented in the $\Delta C$-dew point calibration table.

BRIEF DESCRIPTION OF THE DRAWINGS

These and other features of the invention will be understood from the description below, taken together with the background art and the Figures herein representing illustrative embodiments and operation of the invention, wherein

FIG. 2 is a table showing humidity as a function of temperature and dew point;

DETAILED DESCRIPTION

Figure 1:
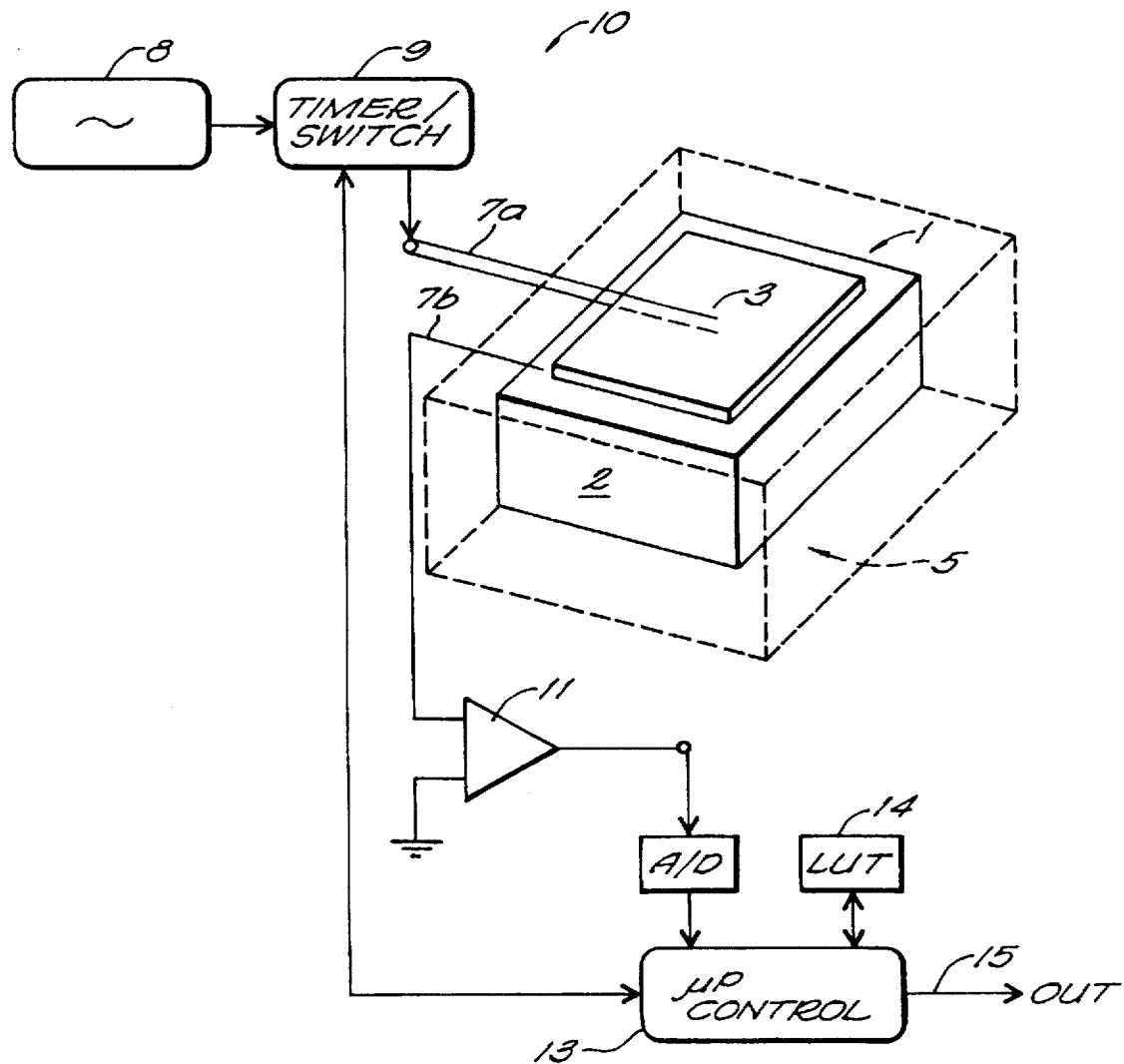
FIG. 1 illustrates a prior art humidity sensor.

FIG. 1 shows a general schematic drawing of a humidity sensor applicable to the present invention and to the prior art. As shown, the system 10 includes a sensing element 1 comprising at least a substrate 2 and an active humidity sensing layer 3, and an environmental chamber 5 illustrated in phantom in which the sensing element 1 resides. Electrodes 7a, 7b connect to opposing sides of the active layer 3 which, as illustrated is a thin film which responds to humidity in the environment. The sensing element 1 is placed in a measurement circuit which, simply by way of example, is illustrated as including an oscillating signal source 8, a timer and switching unit 9, such as a flip flop or microprocessor controlled switch or switch array, and an amplifier 11 which may be operated in various embodiments synchronously or with a partial duty cycle to produce an output signal representative of the capacitance or other electrical characteristic of the sensor 1. As shown in FIG. 1, this output is digitized and fed to a microprocessor or controller 13 which compares the output signal to signals stored in a look-up table 14 and determines the corresponding values of relative humidity or dew point to which the sensor is subjected. This humidity value is produced as an output signal on line 15 and may for example be fed to a panel display or be output to a printer, digital storage device or other form of recorder or display.

In general, the measured sensor property such as capacitance of the active layer 3 will be proportional to the dielectric constant $\epsilon$ of the material times its surface area divided by its thickness, and as noted above, the thickness is generally small, well under one mil to assure a fast response time. For alumina or typical polymer films, a dielectric constant $\epsilon$ is about 3 to 5, while that of water is 81, so that as water is gained or lost in the active layer, the capacitance of the element will increase or decrease respectively. In general, the level of moisture in the plastic film will be proportional to the pressure of moisture in the air and will also be a function of surrounding temperature. The final output may be calibrated either in absolute terms of grams of water per cubic meter, as a partial pressure of water vapor in the total gas, or as a dew point measurement; that is, as a temperature T at which the saturated water vapor pressure would be equal to the measured water vapor pressure. The moisture measurement may also be reported out in relative units, i.e. as a relative humidity.

FIG. 2 shows a representative portion of a table of aqueous vapor pressure over ice in millimeters of mercury for a temperature range of 0 to 20 degrees centigrade. These empirical tables are conventionally used for straightforward conversions between the various forms of humidity output measurement. However, as an initial step, the capacitance of the sensor must be compiled over the expected range of temperature and humidity operating conditions.

As applied to a sensor described above, a typical film capacitance may be around 200 pF at zero humidity, and would generally rise with increasing water vapor in the surrounding air. In general, the taking in or release of water may be physically modeled as an equilibrium process going on at the surface of the polymer sensing film, between water molecules on the surface having a relatively low energy and water molecules in the surrounding vapor. In general, the energy of water molecules in the gas is higher, and the bound molecules are able to escape from the surface as the temperature rises and a greater proportion of the surface molecules acquire a higher energy.

The saturation pressure may be represented as $P_S = P_{S_o} e^{\Delta E_1 / RT}$ where $\Delta E_1$ corresponds to the difference in energy of a free water molecule and a bound (liquid) molecule, and R is the Boltzmann constant. Because of this equilibrium process, while the saturation pressure of humidity in a gas will increase sharply with temperature, the capacitance of the sensor will decrease with temperature due to the shift in distribution between liquid and gaseous water, decreasing the amount of water residing in or on the sensing film. The horizontal asymptote makes it difficult to obtain accurate readings at high temperatures and saturation.

The general form of these curves is a nested family of curves, which are invertible, in the sense that a capacitance reading at a known temperature can be converted to a specific humidity or dew point value.

Figure 3:
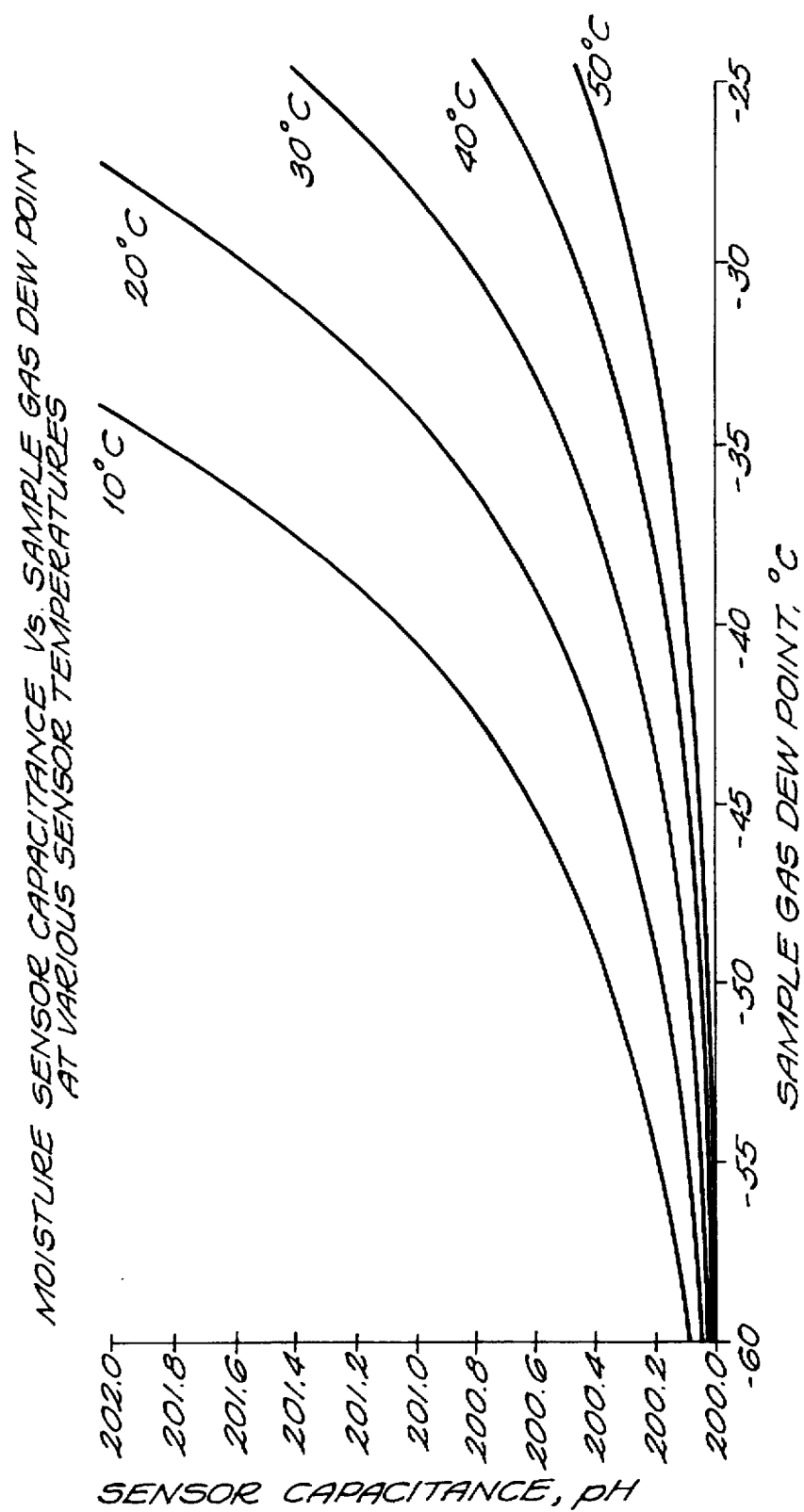
FIG. 3 is a graph showing sensor capacitance as a function of dew point at various temperatures.
Figure 3A:
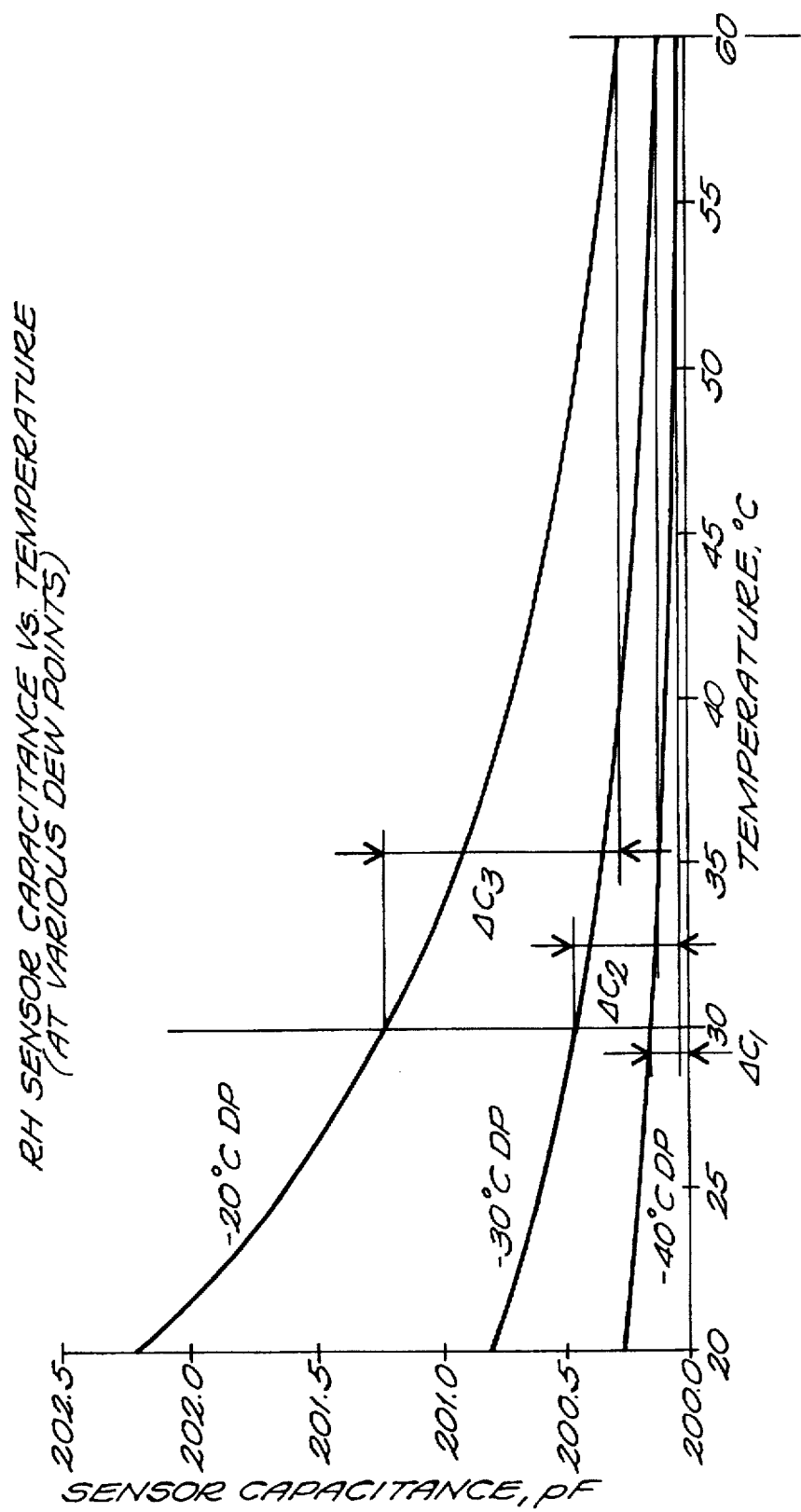
FIG. 3A is a graph showing sensor capacitance as a function of temperature at various dew points.

As noted above, the humidity sensor resistance and/or capacitance is a function of both humidity and temperature. This function is customarily represented as a family of capacitance vs. gas dew point curves for a set of different temperatures, as shown in FIG. 3, or capacitance vs. temperature curves for several different sample gas dew point values as shown in FIG. 3A. The gas temperature may be assumed to coincide with the sensor temperature at least on the sensor surface.

Empirical tables of aqueous vapor pressure over ice at different temperatures as shown in FIG. 2 are conventionally used for straightforward conversions between the various units of humidity output measurement. Using such tables, the capacitance vs. dew point and temperature function as shown in FIG. 3 and FIG. 3A can be transformed into capacitance vs. pressure, relative humidity or any other unit of moisture measurement which is desired for the measurement application involved. An additional parameter may be measured for effecting some of these conversions, and this is readily provided by a separate sensor, such as a pressure sensor. For example a gas pressure reading is needed to transform dew point or partial pressure into units of grams per kilogram.

However, as an initial step, the capacitance of the sensor vs. humidity/temperature function must first be empirically obtained over the range of expected operating conditions, and must be represented in terms of at least one of the units of the moisture measurement.

FIG. 3 shows a typical such family of calibration curves for effecting prior art measurement, with sensor capacitance in picofarads plotted against sample gas dew point, for a range gas temperatures between ten and fifty degrees. Using these stored curves, measured sensor capacitance is readily converted, for a given gas temperature, into a dew point measurement of sample gas, and this, in turn may be converted using a table (FIG. 2) to an absolute or relative humidity measurement. Other curves may be used in particular ranges of conditions to simplify measurements, such as capacitance vs. relative humidity, which is largely temperature-independent in a restricted range of conditions.

The aforementioned drifts due to sensor aging, hysteresis and systematic errors of the measurement instrument affect the actual sensor response curve by shifting the family of curves shown in FIG. 3 upward or downward. This shift is substantially isometric—that is, it translates the curve without changing its shape or distance between points along the curve. In practical terms such calibration curve drift results in measurement error of about ±1% or more for a commercially available relative humidity sensor. A similar shift occurs in the calibration curves expressed in other common units.

In one embodiment of the invention shown in FIG. 3A applicant utilizes as calibration curves an empirically tabulated set of sensor capacitance vs. temperature curves for different dew points. These curves FIG. 3A may be regarded as a "vertical slice" of the curve family shown in FIG. 3.

As can be seen in FIG. 3A, the vertical distance between two points on each curve, represented by sensor capacitance increment $\Delta C$ and taken at two different temperatures (30° C. and 60° C. in FIG. 3A), will remain the same in spite of the upward/downward drift of a curve. At the same time, the increment ΔC between two fixed temperature points is an increasing function of dew point. More generally, a one-to-one correlation between capacitance increment and dew point can be established at any two given temperature points within the range of expected operating conditions.

Applicant uses this correspondence to initially establish by direct measurement and tabulation, and then apply, a family of calibration curves to obtain differential measurements which are unaffected by "aging" and other sources of error mentioned above. Using this capacitance increment measurement technique a cumulative relative humidity measurement error of less that ±0.02% has been achieved over a one year time without re-calibration. Applicant exploits this property in new measurement protocols, and corresponding apparatus, shown in FIGS. 4, 4A and 5. The apparatus drives the sensor between two temperatures and develops a ΔC measurement, which is then converted via the stored calibration curves.

Figure 4:
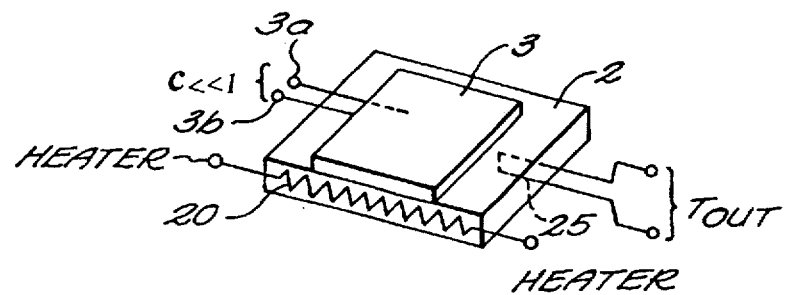
FIGS. 4 and 4A illustrate sensor embodiments of the invention with a heater and a cooler, respectively.

FIG. 4 shows a sensor in accordance with the present invention for improved humidity detection. As shown, the sensor includes a sensing film 3 on a substrate or support 2 wherein electrode contacts 3a, 3b are provided to the upper and lower surfaces of the sensor. A heating element 20 which may for example be formed by a metalized film within the body of or on the surface of support 2 is adapted to provide heat to the assembly for driving the temperature upward, while a thermocouple or other temperature sensing device 25 is formed on or mounted in close proximity to the sensing element 3 to provide a signal which accurately reflects the temperature at the surface. Other forms of heater control are also contemplated. For example, when using a thin platinum film as the heater, temperature control may be achieved by placing the heater in a bridge with two different precision resistors, e.g., via a switch or switch array operating under control of a microprocessor. The resistance values are selected such that their resistance is equivalent or proportional to that of the heater resistance at the specified temperature $T_1$ or $T_2$, and the imbalance voltage developed across the bridge controls the gain of a power supply connected to the heater, so that power is provided to the heater in proportion to its variation from this set resistance value. Thus, the platinum heater is powered until it reaches the desired resistance set point. At this point the computer switches in the other resistor and powers the heater to reach a different temperature. The platinum film lies closely under or may be deposited on one surface of, the sensing film and thus accurately represents the sensing film temperature, although, as noted above, one or more thermocouples may be provided to allow more accurate control, for example to introduce temperature dependent or environment dependent corrections.

Figure 4A:
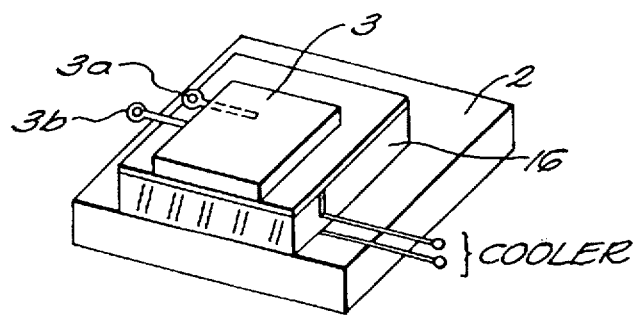

FIG. 4A illustrates another embodiment of a humidity sensor in accordance with the present invention. In this embodiment, a thermoelectric cooler or Peltier effect cooler 16 is provided as the support for the sensing film 3. As before, surface electrodes are provided for detection of changes in the sensor capacitance and a temperature sensor (not shown) may be mounted in an appropriate position to allow determination of the surface temperature. It will be understood that several thermocouples may be provided to allow an automated controller to detect a temperature gradient and extrapolate or interpolate the actual surface temperature. The invention also contemplates embodiments where both a cooler and a heater are provided and each may be energized at different times to separately drive the temperature up or down. It will be understood that each sensor is to be employed in a system wherein an electric circuit or microprocessor controller sets the two different temperatures $T_1$ and $T_2$ to which the relative humidity sensor will be driven and controls another circuit as discussed above, to measure capacitance.

It will further be understood that when a thermoelectric cooler is provided for the sensor, heating may be simply accomplished by reversing the current direction to reverse the heat-cold temperature distribution in the cooler element. Thus, for example, a preset current, for example 200 mA may be continuously supplied to the cooler element and the temperature change may be achieved by reversing the current polarity. At one current direction the sensor is cooled below ambient temperature, while a reversal of current causes the thermoelectric element 16 to work as a heat pump and increase the temperature of the sensor. By monitoring the thermocouple output, the current may be reversed, and sensor capacitance measurements taken at appropriate times.

Figure 5:
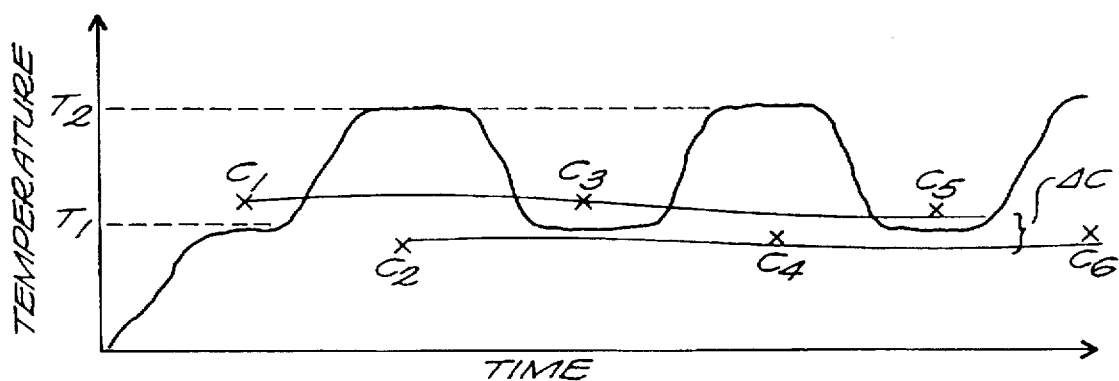
FIG. 5 illustrates a system operating according to the method of the present invention.

FIG. 5 shows the general form of capacitance measurement effected by the present invention. Temperature of the sensor is plotted on the vertical axis against time, and a representative capacitance measurement point indicated in each interval. As the sensor toggles back and forth between temperatures, the sensor capacitance measurement $C_1$, $C_2$, $C_3$ . . . are taken and the processor forms the difference $C_1-C_2$, $C_3-C_4$ . . . as these differences converge to a stable value. The stable value ΔC is then looked up in a previously stored table in which the sensor capacitance difference between these temperatures has been stored for the range of dew points encountered in practice. The processor then outputs the dew point measurement, or the desired equivalent (e.g. relative humidity at ambient) by empirical conversion.

It has been assumed that at least two capacitance measurements are performed at two different temperatures but with the same sample gas portion or at least at the same moisture contents. To avoid dynamic error when the moisture concentration is changing in time, moisture sensors with relatively small time response are preferably used, so that the temperature change of the sensor and two consecutive measurements before and after this change thus can be made in a short period of time. One suitable sensor is the commercially available MiniCap2 sensor sold by Panametrics, Inc. of Waltham, Mass. These sensors have a response time less than two seconds in the range of 0° to 180° C., and their small size allows the required temperature change and two consecutive capacitance measurements to be made in about a 5 to 20 second time interval using a relatively low power heater, less than one Watt. In most cases this is fast enough for dynamic error to be neglected.

More sophisticated data processing algorithms utilizing more than two data points are also known to those experienced in the field of instrumentation and can be appropriately used with this invention in order to minimize dynamic error. Thus the invention further contemplates systems wherein automated numerical filtering, averaging, fitting, convergence or estimation protocols are applied to the data points, for example with digital measurement signal processing to develop a precise ΔC measurement, or to correct the measured humidity value in the presence of changing temperature, pressure or humidity conditions.

Furthermore, while the foregoing description relates to a measurement wherein the sensor characteristic is measured at two temperatures and the difference is converted, via stored curves, to a humidity measurement, the salient feature of the invention lies in the accuracy of this measurement, since any shifting or drift, whether due to sensor aging, stray capacitance or other common effect, is canceled by the differencing step.

In a further aspect of the invention, the measurement so taken is applied to update or recalibrate a conventional system, such as a single-point sensor system employing the calibration curves of FIG. 3. According to this aspect, a microprocessor controller controls the temperature driver to perform a ΔC measurement, then compares the humidity value with the values given by the stored curves for a single-temperature sensor reading. The error function is applied to update the stored curves, which may involve simply shifting the curve up or down, after which the system then continues to operate in a single-temperature reading mode for a period of days, weeks or months. As noted above, the ΔC correction protocol may be quickly implemented to provide a corrective shift of a single measurement curve in a few seconds. Such a correction protocol obviates the various calibration or correction protocols required in the prior art, such as the periodic provision of a calibration sample gas at known relative humidity.

The invention has been described with reference to specific embodiment and preferred implementations shown in the FIGURES above. However, it will be understood that a great many circuit, control systems and methods and devices for operation and correction of humidity sensors have been developed in the past and are all usable with, and may be incorporated with the improved method and sensors of the present invention. The invention being thus disclosed and described, further variations and modifications will occur to those skilled in the art, and all such modifications and variations are considered to be within the scope of the invention, as set forth in the claims appended hereto.

What is claimed is:

1. A humidity sensing apparatus for measuring humidity, such apparatus comprising a sensor element having a humidity responsive surface film which responds to surrounding humidity by changing an electrical characteristic including at least one of resistance and capacitance said sensor element including electrodes for placing said sensor element in a detection circuit to detect said electrical characteristic said sensor element being adapted for insertion in a sensing environment to respond to moisture in the environment, and further including a thermal control assembly configured to drive said sensor element between a first temperature $T_1$ and a different second temperature $T_2$ as said electrical characteristic is measured such that output of said apparatus is the thermal coefficient of said electrical characteristic, said thermal coefficient thereby providing a stable and accurate measure of said moisture in the environment by reference to a stored table of coefficients.

2. A humidity sensing apparatus according to claim 1, wherein said thermal control assembly is configured to drive said sensor element between first and second temperatures and includes a controller, and a thermal drive element controlled by the controller.

3. A humidity sensing apparatus according to claim 2, wherein said thermal drive element includes at least one of a heater and a cooler.

4. A humidity sensing apparatus according to claim 3, wherein said thermal drive element includes both a heater and a cooler.

5. A humidity sensing apparatus according to claim 3, further comprising storage means for storing a table of thermal coefficients, and means for determining humidity by looking up the measured thermal coefficient in the table.

6. A humidity sensing apparatus according to claim 5, wherein said table is a table of differences in said electrical characteristic between temperatures $T_1$ and $T_2$ for a range of dew points.

7. A humidity sensing apparatus according to claim 5, wherein said table is a table of thermal coefficients of said electrical characteristic for a range of humidity measurements.

8. A method of making a moisture measurement, such method comprising the steps of providing a humidity sensing element having an electrical resistance or capacitance characteristic which varies in accordance with surrounding humidity driving said humidity sensing element so that it cycles between a first temperature $T_1$ and a second temperature $T_2$ which differs from $T_1$ measuring the thermal coefficient of said electrical characteristic between said temperatures $T_1$ and $T_2$, and comparing the measured thermal coefficient to a table of stored thermal coefficient measurements of said characteristic of the sensing element to determine the humidity.

9. The method of making a moisture measurement according to claim 8, further comprising the step of previously compiling and storing a table of thermal coefficients of said electrical characteristic of the humidity sensing element as a function of humidity, and wherein the step of comparing includes looking up said measured thermal coefficient in said previously-compiled table to determine said humidity measurement.

10. The method of making a moisture measurement according to claim 8, wherein the step of driving said sensing element between a first temperature $T_1$ and a different temperature $T_2$ is effected by heating the sensing element.

11. The method of making a moisture measurement according to claim 8, wherein the step of driving said sensing element between a first temperature $T_1$ and a second temperature $T_2$ is effected by cooling the sensing element.

12. The method of making a moisture measurement according to claim 8, wherein the step of driving The sensing element between a first temperature $T_1$ and a second temperature $T_2$ is achieved by providing both a heater and a cooler, and controlling at least one of the heater or cooler to drive the element between said temperatures $T_1$ and $T_2$.

13. The method of making a moisture measurement according to claim 12, wherein the step of driving the sensing element between a temperature $T_1$ and temperature $T_2$ includes the step of providing power to at least one of the heater or the cooler to drive the sensing element to one of said temperatures away from ambient temperature, and allowing the sensing element to passively return toward ambient temperature.

14. An improved method of measuring humidity, such method comprising the steps of sensing a humidity-responsive value of an electrical resistance or capacitance characteristic of a sensor and converting a sensed characteristic to a humidity measurement via a stored table, wherein the improvement comprises the steps of storing a table of differential measurements corresponding to thermal coefficients of said humidity-responsive electrical characteristic of the sensor, and thereafter measuring humidity by sensing said electrical characteristic at two different temperatures to determine a difference measurement and comparing the difference measurement to said stored table of thermal coefficients to thereby effect an accurate measure of humidity.

15. The improved method of claim 14, wherein the step of sensing at two different temperatures is performed by driving said sensor between said temperatures to obtain said difference measurement.

16. The improved method of claim 14, further comprising the step of performing a single temperature measurement by sensing said characteristic at one temperature and comparing the sensed value to a stored reference table of values of said characteristic.

* * * * *